United States Patent
Fort et al.

(10) Patent No.: US 9,107,830 B2
(45) Date of Patent: *Aug. 18, 2015

(54) INHIBITORS OF CRYSTALLIZATION IN A SOLID DISPERSION

(75) Inventors: James J. Fort, Midlothian, VA (US); Steven L. Krill, Gurnee, IL (US); Devalina Law, Libertyville, IL (US); Yihong Qiu, Gurnee, IL (US); Eric A. Schmitt, Libertyville, IL (US)

(73) Assignee: ABBVIE, INC., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/691,819

(22) Filed: Mar. 27, 2007

(65) Prior Publication Data
US 2007/0249692 A1    Oct. 25, 2007

Related U.S. Application Data

(63) Continuation of application No. 09/438,994, filed on Nov. 12, 1999, now abandoned.

(51) Int. Cl.
| A61K 9/20 | (2006.01) |
| A61K 9/48 | (2006.01) |
| A61K 31/427 | (2006.01) |
| A61K 9/16 | (2006.01) |
| A61K 31/497 | (2006.01) |

(52) U.S. Cl.
CPC ............. *A61K 9/1635* (2013.01); *A61K 9/1652* (2013.01); *A61K 9/2027* (2013.01); *A61K 9/2054* (2013.01); *A61K 9/4866* (2013.01); *A61K 31/427* (2013.01); *A61K 31/497* (2013.01)

(58) Field of Classification Search
CPC ... A61K 9/1635; A61K 9/207; A61K 9/1652; A61K 31/427; A61K 31/497; A61K 9/1614
See application file for complete search history.

(56) References Cited

U.S. PATENT DOCUMENTS

| 4,758,427 A | 7/1988 | Leeson |
| 4,769,235 A | 9/1988 | Schlesinger et al. |
| 4,769,236 A | 9/1988 | Panoz et al. |
| 4,801,460 A | 1/1989 | Goertz et al. |

(Continued)

FOREIGN PATENT DOCUMENTS

| CA | 2227272 | 3/1997 |
| CA | 2 343 234 | 3/2000 |

(Continued)

OTHER PUBLICATIONS

U.S. Appl. No. 09/709,829, filed Nov. 10, 2000, Fort et al.

(Continued)

*Primary Examiner* — Lakshmi Channavajjala
(74) *Attorney, Agent, or Firm* — J.A. Lindeman & Co., PLLC

(57) ABSTRACT

A pharmaceutical composition is disclosed which comprises a solid dispersion of a pharmaceutical compound in a water soluble carrier, such as polyethylene glycol (PEG), and a crystallization inhibitor, such as polyvinylpyrrolidone or hydroxypropylmethylcellulose. The solid dispersion may optionally be encapsulated in hard gelatin capsules, compressed into a tablet, or may be granulated with a pharmaceutically acceptable granulating agent. Also disclosed are methods of making said solid dispersion and methods of treatment employing said solid dispersion.

14 Claims, 15 Drawing Sheets

(56) References Cited

U.S. PATENT DOCUMENTS

| | | |
|---|---|---|
| 4,851,438 A | 7/1989 | Flashinski |
| 4,880,585 A | 11/1989 | Klimesch et al. |
| 4,904,699 A | 2/1990 | Bauer |
| 4,957,681 A | 9/1990 | Klimesch et al. |
| 4,996,058 A | 2/1991 | Sinnreich |
| 5,073,379 A | 12/1991 | Klimesch et al. |
| 5,145,683 A | 9/1992 | Rhodes |
| 5,368,864 A | 11/1994 | Lahr et al. |
| 5,405,616 A | 4/1995 | Wunderlich et al. |
| 5,456,923 A | 10/1995 | Nakamichi et al. |
| 5,490,990 A | 2/1996 | Grabowski et al. |
| 5,525,628 A | 6/1996 | Nicola et al. |
| 5,541,206 A | 7/1996 | Kempf et al. |
| 5,545,628 A | 8/1996 | Deboeck et al. |
| 5,552,159 A | 9/1996 | Mueller et al. |
| 5,559,158 A | 9/1996 | Al-Razzak et al. |
| 5,567,823 A * | 10/1996 | Tien et al. ............. 548/204 |
| 5,610,193 A | 3/1997 | Al-Razzak et al. |
| 5,635,523 A | 6/1997 | Kempf et al. |
| 5,641,516 A | 6/1997 | Grabowski et al. |
| 5,648,497 A | 7/1997 | Kempf et al. |
| 5,674,882 A | 10/1997 | Kempf et al. |
| 5,725,878 A | 3/1998 | Al-Razzak et al. |
| 5,727,878 A | 3/1998 | Sullivan, Jr. |
| 5,741,519 A | 4/1998 | Rosenberg et al. |
| 5,773,025 A | 6/1998 | Baichwal |
| 5,776,495 A | 7/1998 | Duclos et al. |
| 5,834,472 A | 11/1998 | Sangekar et al. |
| 5,889,051 A | 3/1999 | Chen et al. |
| 5,897,910 A | 4/1999 | Rosenberg et al. |
| 5,914,332 A | 6/1999 | Sham et al. |
| 5,939,099 A | 8/1999 | Grabowski et al. |
| 5,945,123 A | 8/1999 | Hermelin |
| 5,945,127 A | 8/1999 | Breitenbach et al. |
| 5,948,426 A | 9/1999 | Jefferies |
| 5,948,436 A | 9/1999 | Al-Razzak et al. |
| 5,955,475 A | 9/1999 | Krape et al. |
| 5,969,181 A | 10/1999 | Breitenbach et al. |
| 6,001,391 A | 12/1999 | Zeidler et al. |
| 6,009,690 A | 1/2000 | Rosenberg et al. |
| 6,027,747 A | 2/2000 | Terracol et al. |
| 6,037,157 A | 3/2000 | Norbeck et al. |
| 6,042,847 A * | 3/2000 | Kerc et al. ............. 424/472 |
| 6,045,829 A | 4/2000 | Liversidge et al. |
| 6,063,821 A | 5/2000 | Breitenbach et al. |
| 6,066,334 A | 5/2000 | Kolter et al. |
| 6,083,518 A | 7/2000 | Lindahl |
| 6,120,802 A | 9/2000 | Breitenbach et al. |
| 6,132,659 A | 10/2000 | Rosenberg et al. |
| 6,150,424 A | 11/2000 | Breitenbach et al. |
| 6,187,342 B1 | 2/2001 | Zeidler et al. |
| 6,197,781 B1 | 3/2001 | Guitard et al. |
| 6,197,787 B1 | 3/2001 | Franson et al. |
| 6,221,368 B1 | 4/2001 | Breitenbach et al. |
| 6,232,333 B1 | 5/2001 | Lipari et al. |
| 6,248,363 B1 | 6/2001 | Patel et al. |
| 6,251,434 B1 | 6/2001 | Breitenbach et al. |
| 6,281,282 B1 | 8/2001 | Breitenbach et al. |
| 6,290,990 B1 | 9/2001 | Grabowski et al. |
| 6,294,192 B1 | 9/2001 | Patel et al. |
| 6,318,650 B1 | 11/2001 | Breitenbach et al. |
| 6,322,816 B1 | 11/2001 | Zeidler et al. |
| 6,350,398 B1 | 2/2002 | Breitenbach et al. |
| 6,383,471 B1 | 5/2002 | Chen et al. |
| 6,387,401 B2 | 5/2002 | Rosenberg et al. |
| 6,423,256 B1 | 7/2002 | Kothrade et al. |
| 6,436,440 B1 | 8/2002 | Meffert et al. |
| 6,451,339 B2 | 9/2002 | Patel et al. |
| 6,462,093 B1 | 10/2002 | Miyamoto et al. |
| 6,465,011 B2 | 10/2002 | Law et al. |
| 6,488,939 B1 | 12/2002 | Zeidler et al. |
| 6,547,997 B1 | 4/2003 | Breitenbach et al. |
| 6,579,521 B2 | 6/2003 | Sahner |
| 6,599,528 B1 | 7/2003 | Rosenberg et al. |
| 6,599,931 B1 | 7/2003 | Breitenbach et al. |
| 6,608,198 B2 | 8/2003 | Dickman et al. |
| 6,632,455 B2 * | 10/2003 | Sangekar et al. ............. 424/486 |
| 6,669,879 B1 | 12/2003 | Spengler et al. |
| 6,669,883 B1 | 12/2003 | Rosenberg et al. |
| 6,692,767 B2 | 2/2004 | Burnside et al. |
| 6,730,319 B2 | 5/2004 | Maeder et al. |
| 6,733,781 B2 | 5/2004 | Abu-Izza et al. |
| 6,737,005 B1 | 5/2004 | Rosenberg et al. |
| 6,787,157 B1 | 9/2004 | Rosenberg et al. |
| 6,834,310 B2 | 12/2004 | Munger et al. |
| 6,894,171 B1 | 5/2005 | Bauer et al. |
| 6,923,988 B2 | 8/2005 | Patel et al. |
| 7,014,810 B2 | 3/2006 | Krull et al. |
| 7,148,359 B2 | 12/2006 | Chemburkar et al. |
| 7,229,641 B2 | 6/2007 | Cherukuri |
| 7,364,752 B1 * | 4/2008 | Fort et al. .................. 424/455 |
| 8,481,081 B2 * | 7/2013 | Babcock et al. ............. 424/488 |
| 2001/0006650 A1 | 7/2001 | Burnside et al. |
| 2001/0039551 A1 | 11/2001 | Saito et al. |
| 2001/0051721 A1 | 12/2001 | Dickman et al. |
| 2002/0006443 A1 | 1/2002 | Curatolo et al. |
| 2002/0114833 A1 | 8/2002 | Abu-Izza et al. |
| 2002/0161884 A1 | 10/2002 | Munger et al. |
| 2002/0187188 A1 | 12/2002 | Cherukuri |
| 2003/0015814 A1 | 1/2003 | Kurll et al. |
| 2003/0021840 A1 | 1/2003 | Infeld et al. |
| 2003/0039686 A1 | 2/2003 | Maeder et al. |
| 2003/0054038 A1 | 3/2003 | Crew et al. |
| 2003/0072801 A1 | 4/2003 | Curatolo et al. |
| 2003/0091630 A1 | 5/2003 | Louie-Helm et al. |
| 2003/0091643 A1 | 5/2003 | Friesen et al. |
| 2003/0096791 A1 | 5/2003 | Gupte et al. |
| 2003/0104063 A1 | 6/2003 | Babcock et al. |
| 2003/0153608 A1 | 8/2003 | Maegerlein et al. |
| 2003/0161884 A1 | 8/2003 | Rosenberg et al. |
| 2004/0001888 A1 | 1/2004 | Jin |
| 2004/0013697 A1 | 1/2004 | Berndl et al. |
| 2004/0013734 A1 | 1/2004 | Babcock et al. |
| 2004/0014817 A1 | 1/2004 | Rosenberg et al. |
| 2004/0029892 A1 | 2/2004 | Rosenberg et al. |
| 2004/0062802 A1 | 4/2004 | Hermelin |
| 2004/0091529 A1 | 5/2004 | Edgren et al. |
| 2004/0096499 A1 | 5/2004 | Vaya et al. |
| 2004/0156905 A1 | 8/2004 | Babcock et al. |
| 2004/0185170 A1 | 9/2004 | Chungi et al. |
| 2004/0258752 A1 | 12/2004 | Paruthi et al. |
| 2005/0003004 A1 | 1/2005 | Vehring et al. |
| 2005/0008706 A1 | 1/2005 | Holm et al. |
| 2005/0025791 A1 | 2/2005 | Remenar et al. |
| 2005/0031691 A1 | 2/2005 | McGurk et al. |
| 2005/0048112 A1 | 3/2005 | Breitenbach et al. |
| 2005/0079138 A1 | 4/2005 | Chickering, II et al. |
| 2005/0084529 A1 | 4/2005 | Rosenberg et al. |
| 2005/0100586 A1 | 5/2005 | Sournac et al. |
| 2005/0143404 A1 | 6/2005 | Rosenberg et al. |
| 2006/0257470 A1 | 11/2006 | Rosenberg et al. |
| 2007/0249643 A1 | 10/2007 | Rosenberg et al. |
| 2007/0249692 A1 | 10/2007 | Fort et al. |
| 2007/0287664 A1 | 12/2007 | Ralston, II et al. |

FOREIGN PATENT DOCUMENTS

| | | |
|---|---|---|
| CA | 2 352 874 | 6/2000 |
| CA | 2 367 020 | 9/2000 |
| CA | 2 368 625 | 10/2000 |
| CA | 2 374 931 | 1/2001 |
| CA | 2408915 | 11/2002 |
| CA | 2 479 749 | 10/2003 |
| CA | 2 501 245 | 4/2004 |
| CA | 2 568 378 | 12/2005 |
| EP | 0 414 422 | 2/1991 |
| EP | 0570327 A1 | 11/1993 |
| EP | 0852140 | 7/1998 |
| EP | 0 864 324 | 9/1998 |
| EP | 0 864 326 | 9/1998 |
| EP | 0 988 106 | 3/2000 |
| EP | 0 732 923 | 12/2001 |
| EP | 0 942 721 | 1/2003 |
| EP | 1 227 797 | 1/2005 |

(56) References Cited

FOREIGN PATENT DOCUMENTS

| | | |
|---|---|---|
| EP | 1227797 | 1/2005 |
| EP | 1 175 205 | 6/2006 |
| EP | 1175205 | 6/2006 |
| GB | 2053681 | 2/1981 |
| GB | 2173703 A | 10/1986 |
| JP | 61205208 | 11/1986 |
| WO | 90/06115 | 6/1990 |
| WO | WO9118613 | 12/1991 |
| WO | WO9311749 A1 | 6/1993 |
| WO | WO9315736 | 8/1993 |
| WO | WO95/07696 | 3/1995 |
| WO | 95/09614 | 4/1995 |
| WO | WO9509614 A1 | 4/1995 |
| WO | 95/22319 | 8/1995 |
| WO | 96/23499 | 8/1996 |
| WO | WO9636318 A2 | 11/1996 |
| WO | 97/01349 | 1/1997 |
| WO | 9706781 | 2/1997 |
| WO | 97/21685 | 6/1997 |
| WO | 97/44014 | 11/1997 |
| WO | 9746222 | 12/1997 |
| WO | 98/07429 | 2/1998 |
| WO | 98/22106 | 5/1998 |
| WO | 98/24430 | 6/1998 |
| WO | WO0000179 | 1/2000 |
| WO | 00/57854 | 10/2000 |
| WO | 00/74677 | 12/2000 |
| WO | 01-00175 | 1/2001 |
| WO | 01/22938 | 4/2001 |
| WO | 01/23362 | 4/2001 |
| WO | 01/34119 | 5/2001 |
| WO | WO0134118 | 5/2001 |
| WO | 01/34118 | 6/2001 |
| WO | 01/52821 | 7/2001 |
| WO | 01/91727 | 12/2001 |
| WO | 02/20057 | 3/2002 |
| WO | 02/092595 | 11/2002 |
| WO | 02089835 | 11/2002 |
| WO | 02/096395 | 12/2002 |
| WO | 03-006382 | 1/2003 |
| WO | 03/006383 | 1/2003 |
| WO | WO03063833 A1 | 8/2003 |
| WO | 03/080120 | 10/2003 |
| WO | WO2004032903 | 4/2004 |
| WO | 2004/039349 | 5/2004 |
| WO | 2004/050068 | 6/2004 |
| WO | 2004/054568 | 7/2004 |
| WO | 2005/004836 | 1/2005 |
| WO | 2005/007139 | 1/2005 |
| WO | 2005/039551 | 5/2005 |
| WO | WO2005/039551 | 5/2005 |
| ZA | 9608134 A | 3/1998 |

OTHER PUBLICATIONS

Awni, W., et al., "Significantly Reduced Food Effect and Pharmacokinetic Variability with a Novel Lopinavir/Ritonavir Tablet Formulation", *third IAS Conf. on HIV Pathogenesis and Treatment*, (2005).

BASF Fine Chemicals, "ExAct Excipients & Actives for Pharma", *BASF*, 2:1-16 (1999).

Bouma, M.G., et al., "Novel Therapetic Delivery Systems", *J. of Contr. Rel.*, 87:199-308 (2003).

Breitenbach, J., "Melt extrusion: from process to drug delivery technology", *Eur. J. of Pharm. & Biopharm.*, 54:107-117 (2002).

Breitenbach, J., "Melt Extrusion Can Bring New Benefits to HIV Therapy: The Example of Kaletra (R) Tablets", *Amer. :J. of Drug Deliv.*, 4(2):61-64 (2006).

Corrigan, O.I. & Healy, A.M., "Surfactants in Pharmaceutical Products and Systems", *Encycl. of Pharm. Tech.*, 2639-2653 (2002).

Forster, A., et al., "Selection of excipients for melt extrusion with two poorly water-soluble drugs by solubility parameter calculation and thermal analysis", *Intn'l J. of Pharm.*, 226:147-161 (2001).

Hulsmann, S., et al., "Melt extrusion—an alternative method for enhancing the eissolution rate of 17β-estradiol hemihydrate", *Eur. J. of Pharm. & Biopharm.*, 49:237-242 (2000).

International Search Report & Written Opinion from PCT/US2004/027401 dated May 8, 2006.

Karanth, H., et al., "Industrially Feasible Alternative Approaches in the Manufacture of Solid Dispersions: A Technical Report", *AAPS PharmSciTech*, 7(4):Art. 87 (2006).

Law, D., et al., "Physicochemical Considerations in the Preparation of Amorphous Ritonavir-Poly(ethylene glycol) 8000 Solid Dispersions", *J. of Pharm. Sci.*, 90(8):1015-1025 (2001).

Law, D., et al., "Ritonavir-PEG 8000 Amorphous Solid Dispersions: In Vitro and in Vivo Evaluations", *J. of Pharm. Sci.*, 93(3):563-570 (2004).

Serajuddin, A.T.M., "Solid Dispersioin of Poorly Water-Soluble Drugs: Early Promises, Subsequent Problems, and Recent Breakthroughs", *J. of Pharm. Sci.*, 88(10):1058-1066 (1999).

Zhu, T., et al., New Tablet Formulation of Lopinavir/Ritonavir is Bioequivalent to the Capsule at a Dose of 800/200 $48^{th}$ *Int. Conf. on Antimic. Agents & Chem. (ICAAC)*, (2005).

Dias, L., et al., "Physical and Oral Dog Bioavailability Evaluatoins of ABT-538: PVP Co-Precipitates", Physical Research Suppl. (0724-8741), 13(9):S-351 PDD7475 (1996).

Dias, L., et al., "Physical and Oral Dog Bioavailability Evaluaiton of ABT-538: PVP Co-Precipitates", poster (1996).

Kempf, D.J., et al., "ABT-538 is a potent inhibitor of human immunodeficiency virus protease and has high oral bioavailability in humans", Proc. Natl. Acad. Sci. USA, 92:2484-2488 (1995).

Martin, D., et al., "Method of Preparing an Orally Bioavailable Solid Formulation of an Insoluble Protease Inhibitor as a Coprecipitate With PVP and Other Excipients", Pharmaceutical Research Suppl. (0724-8741), 13(9):S351 PDD 7474 (1996).

Martin, D., et al., "Method of Preparing an Orally Bioavailability Solid Formulation of an Insoluble Protease Inhibitor as a Coprecipitate with PVP and Other Excipients", Abbott Laboratories (1996).

Breitenbach, Jorg et al., Two Concepts, One Technology: Controlled-Release Solid Dispersions Using Melt Extrusion (Meltrex), Drugs and the Pharmaceutical Sciences vol. 183.

Buhler, Dr. Volker, Polyvinylpyrrolidone Excipients for Pharmaceuticals.

Reexamination Non-Final Office Action for 95/000,568 dated Oct. 28, 2010.

Reexamination Action Closing Prosecution for 95/000,568 dated May 19, 2011.

Reexamination Patent Owner's Comments After Action Closing Prosecution for 95/000,568 dated Jun. 17, 2011.

Opposition Filed by CIPLA on Indian Application No. 726/MUMNP/2009 dated Aug. 11, 2011.

Opposition Filed by Matrix Laboratories on Indian Application No. 726/MUMNP/2009 dated Aug. 11, 2011.

Opposition Filed by Matrix Laboratories on Indian Application No. 676/MUMNP/2007 dated Apr. 28, 2011.

Opposition Filed by Matrix Laboratories on Indian Application No. 677/MUMNP/2007 dated Apr. 28, 2011.

Opposition Filed by Matrix Laboratories on Indian Application No. 1638/MUMNP/2007 dated Apr. 28, 2011.

Hancock B.C., et al., "Characteristics and Significance of the Amorphous State in Pharmaceutical Systems," Journal of Pharmaceutical Sciences, 1997, vol. 86 (1), pp. 1-12.

Royall, P.G., et al., "Characterisation of the Glass Transition of an Amorphous Drug Using Modulated DSC", Pharmaceutical Research, 15(7):1117-1121 (1998).

Serajuddin A.T.M., "Solid Dispersion of Poorly Water-Soluble Drugs: Early Promises, Subsequent Problems, and Recent Breakthroughs," Journal of Pharmaceutical Sciences, 1999, vol. 88 (10), pp. 1058-1066.

Opposition Response to Indian Patent Office dated Aug. 2, 2010 (Opponent: I-MAK, Cipla Limited, Okasa Prive Limited and Matrix Laboratories Limited).

Office Action from EP Application No. 04816820.7 dated Jan. 10, 2007.

(56) References Cited

OTHER PUBLICATIONS

Response to Office Action for EP Application No. 04816820.7 dated Apr. 4, 2008.
Response to Office Action EP Application No. 04816820.7 dated Aug. 10, 2009.
Office Action for U.S. Appl. No. 11/939,640 dated Apr. 8, 2010.
Final Office Action for U.S. Appl. No. 11/939,640 dated Dec. 22, 2010.
Request for Reexamination on Patent No. 7,364,752 (95/000,568) dated Aug. 25, 2010.
Reexam Office Action for U.S. Appl. No. 95/000,568 dated Oct. 28, 2010.
Reexam Action Closing Prosecution for U.S. Appl. No. 95/000,568 dated May 19, 2011.
Reexam Patent Owner's Amendment and Response for U.S. Appl. No. 95/000,568 dated Jun. 17, 2011.
Sinha, S., et al., "Solid Dispersion as an Approach for Bioavailability Enhancement of Poorly Water-Soluble Drug Ritonavir," AAPS PharmSciTech, 2010, vol. 11(2), pp. 518-527.
Ansel, Howard C. et al., Pharmaceutical Dosage Forms and Drug Delivery Systems, Seventh Edition (1999) pp. 367-369.
Breitenbach, Jorg et al., Two Concepts, One Technology: Controlled-Release Solid Dispersions Using Melt Extrusion (Meltrex), Drugs and the Pharmaceutical Sciences vol. 183, p. 179-185, 2008.
Buhler, Dr. Volker, Polyvinylpyrrolidone Excipients for Pharmaceuticals, Sep. 1965.
Forster, Angus et al, Characterization of glass solutions of poorly water-soluble drugs produced by melt extrusion with hydrophilic amorphous polymers, J. Pharmacy and Pharmacology (2001), pp. 303-315, 53(3).
Rowe, Handbook of Pharmaceutical Excipients, Polyoxyethylene Castor Oil Derivatives (2002), pp. 474-478.
Law et al., J. Pharm. Sci., "Ritonavir—PEG 8000 Amorphous Solid Dispersions: In Vitro and in Vivo Evaluations" 93(3): 563-570 (Mar. 2004).
Law et al.,J.Pharm.Sciences, "Physicochemical Considerations in the Preparation of Amorphous Ritonavir-Poly(ethylene glycol) 8000 Solid Dispersions" 90(8): 1015-1025 (Aug. 2001).
U.S. Appl No. 09/709,829, filed Nov. 10, 2000, Fort et al.
U.S. Appl. No. 09/438,994, filed Nov. 12, 1999, Fort et al.
B.J. Aungst et al., "Amphiphilic vehicles improve the oral bioavailability of a poorly soluble HIV protease inhibitor at high doses," Internal Journal of Pharmaceutics 156:79-88 (1997).
B.J. Aungst, et al. "Improved Oral Bioavailability of an HIV Protease Inhibitor Using Celucire 44/14 and Labrasol Vehicles", B.T. Gattetosse 87:49-56 (1994).
W.L. Chiou et al., "Pharmaceutical Applications of Solid Disperson Systems", Journal of Pharmaceutical Sciences60(9): 1281-1302 (1971).
J.L. Ford, "The Current Status of Solid Dispersions", Pharm Acta Helv. 61(3):69-88 (1986).
Palmier et al., S.T.P. Pharma Sciences, pp. 188-194 (1996).
Physicians Desk Reference, online excert, PDR Electronic Library, May 19, 2003.
Physicians Desk Reference, online . . . Norvir, Fenofibrate, and Greiseosulvin, Aug. 2, 2000.

* cited by examiner

INHIBITORS OF CRYSTALLIZATION IN A SOLID DISPERSION

This application is a continuation of U.S. patent application Ser. No. 09/438,994, filed Nov. 12, 1999, now abandoned, which is incorporated herein by reference in its entirety.

TECHNICAL FIELD OF THE INVENTION

The instant invention relates to the fields of pharmaceutical and organic chemistry, and provides novel solid dispersion pharmaceutical formulations which demonstrate an inhibition of crystallization.

BACKGROUND OF THE INVENTION

One measure of the potential usefulness of an oral dosage form of a pharmaceutical agent is the bioavailability observed after oral administration of the dosage form. Various factors can affect the bioavailability of a drug when administered orally. These factors include aqueous solubility, drug absorption throughout the gastrointestinal tract, dosage strength, and first pass effect. Aqueous solubility is one of the most important of these factors. When a drug has poor aqueous solubility, attempts are often made to identify salts or other derivatives of the drug which have improved aqueous solubility. When a salt or other derivative of the drug is identified which has good aqueous solubility, it is generally accepted that an aqueous solution formulation of this salt or derivative will provide the optimum oral bioavailability. The bioavailability of the aqueous oral solution formulation of a drug is then generally used as the standard or ideal bioavailability against which other oral dosage forms are measured.

For a variety of reasons, including patient compliance and taste masking, a solid dosage form, such as a capsule or tablet, is usually preferred over a liquid dosage form. However, oral solid dosage forms of a drug generally provide a lower bioavailability than oral solutions of the drug. One goal of the development of a suitable solid dosage form is to obtain a bioavailability of the drug that is as close as possible to the ideal bioavailability demonstrated by the oral aqueous solution formulation of the drug.

An alternative dosage form is a solid dispersion. The term solid dispersion refers to the dispersion of one or more active ingredients in an inert carrier or matrix at solid state prepared by the melting (or fusion), solvent, or melting-solvent methods. (Chiou and Riegelman, *Journal of Pharmaceutical Sciences*, 60, 1281 (1971)). The dispersion of a drug or drugs in a solid diluent by mechanical mixing is not included in this category. Solid dispersions may also be called solid-state dispersions.

Retroviral protease inhibiting compounds are useful for inhibiting HIV proteases in vitro and in vivo, and are useful for inhibiting HIV (human immunodeficiency virus) infections and for treating AIDS (acquired immunodeficiency syndrome). HIV protease inhibiting compounds typically are characterized by having poor oral bioavailability. Examples of HIV protease inhibiting compounds include 2S,3S,5S)-5-(N—(N—((N-methyl-N-((2-isopropyl-4-thiazolyl)methyl)amino)carbonyl)L-valinyl)amino-2-(N-((5-thiazolyl)methoxy-carbonyl)-amino)-amino-1,6-diphenyl-3-hydroxyhexane(ritonavir);
(2S,3S,5S)-2-(2,6-Dimethylphenoxyacetyl)amino-3-hydroxy-5-[2S-(1-tetrahydro-pyrimid-2-onyl)-3-methyl butanoyl]-amino-1,6-diphenylhexane (ABT-378);
N-(2(R)-hydroxy-1(S)-indanyl)-2(R)-phenylmethyl-4(S)-hydroxy-5-(1-(4-(3-pyridylmethyl)-2(S)—N'-(t-butylcarboxamido)-piperazinyl))-pentaneamide(indinavir);
N-tert-butyl-decahydro-2-[2(R)-hydroxy-4-phenyl-3(S)-[[N-(2-quinolylcarbonyl)-L-asparaginyl]amino]butyl]-(4aS,8aS)-isoquinoline-3(S)-carboxamide(saquinavir);
5(S)—Boc-amino-4(5)-hydroxy-6-phenyl-2(R) -phenylmethylhexanoyl-(L)-Val-(L)-Phe-morpholin-4-ylamide;
1-Naphthoxyacetyl-beta-methylthio-Ala-(2S,3S)-3-amino-2-hydroxy-4-butanoyl 1,3-thiazolidine-4-t-butylamide;
5-isoquinolinoxyacetyl-beta-methylthio-Ala-(2S,3S)-3-amino-2-hydroxy-4-butanoyl-1,3-thiazolidine-4-t-butylamide;
[1S-[1R—(R-),2S*])—N$^1$[3-[[[(1,1-dimethylethyl)amino] carbonyl](2-methylpropyl)amino]-2-hydroxy-1-(phenylmethyl)propyl]-2-[(2-quinolinylcarbonyl)amino]-butanediamide;
VX-478; DMP-323; DMP-450; AG1343(nelfinavir);
BMS 186,318; SC-55389a; BILA 1096 BS; and U-140690, or combinations thereof.

While some drugs would be expected to have good solubility in organic solvents, it would not necessarily follow that oral administration of such a solution would give good bioavailability for the drug.

Polyethylene glycol (PEG) solid dispersion formulations are generally known to improve the dissolution and bioavailability of many compounds. However, Aungst et al. has recently demonstrated that this was unable to improve the bioavailability of an HIV protease inhibitor with a cyclic urea structural backbone, called DMP 323 (Aungst et al., *International Journal of Pharmaceutics*, 156, 79 (1997)).

In addition, some drugs tend to form crystals when placed in solution, which can be problematic during formulation.

Polyvinylpyrrolidone (PVP) is known to inhibit crystallization of drugs (Yohioka, M. et al., J. Pharm. Sci., 84, 983, 1995). However, prior to the instant invention, the incorporation of PVP into a second polymer matrix, such as polyethylene glycol, has never been established.

U.S. Pat. No. 4,610,875 teaches a process for the preparation of a stable pharmaceutical dipyridamole composition containing PVP.

U.S. Pat. No. 4,769,236 teaches a process for the preparation of a stable pharmaceutical composition with a high dissolution rate in the gastrointestinal tract containing PVP, wherein the pharmaceutical agent is hydroflumethiazide, dipyridamole, hydrochlorothiazide, cyclothiazide, cyclopenthiazide, polythiazide, methyldopa, spironolactone, quinidine, cyanidol, metronidazole, ibuprofen, naproxen, erythromycin, glaphenin, furosemide, suloctidil, nitrofurantoin, indomethacin, flavoxate, phenobarbitol, cyclandelate, ketoprofen, natridrofuryl, or triamterene.

Thus, it would be a significant contribution to the art to provide a stable solid dispersion pharmaceutical formulation which demonstrates a lack of crystallization.

SUMMARY OF THE INVENTION

The instant invention provides a stable solid dispersion pharmaceutical formulation comprising a pharmaceutical compound, a water soluble carrier, such as polyethylene glycol (PEG), and a crystallization inhibitor, such as polyvinylpyrrolidone (PVP) or hydroxypropylmethylcellulose (HPMC).

Also provided by the instant invention is a pharmaceutical composition comprising a stable solid dispersion as described above with additional pharmaceutically acceptable carriers, diluents, or excipients.

Additionally provided by the instant invention is a method for preparing a stable solid dispersion as described above.

The instant invention still further provides methods of treatment comprising administering an effective amount of a stable solid dispersion as described above to a mammal in need of such treatment.

DETAILED DESCRIPTION OF THE INVENTION

Figure 1:
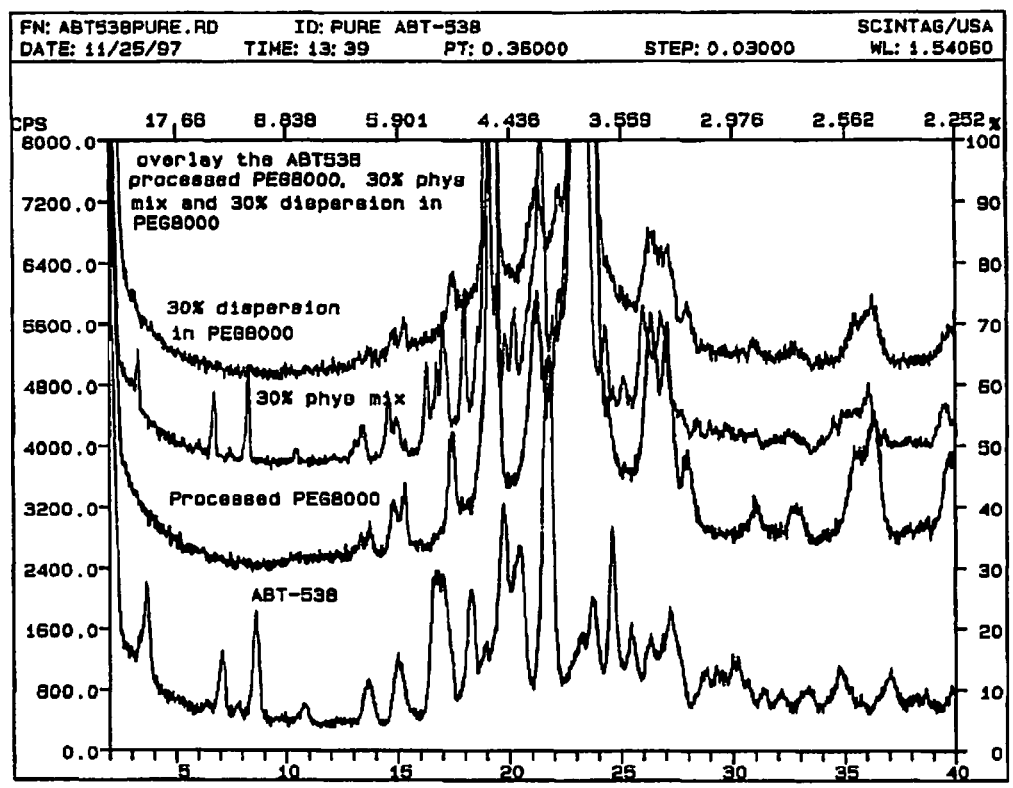
FIG. 1 illustrates the PXD patterns showing that Amorphous ABT-538 can be isolated within PEG alone.

This invention pertains to the preparation of solid dispersion systems for pharmaceuticals which demonstrate a lack of crystallization.

The invention involves dispersion in a hydrophilic matrix of pharmaceuticals which exhibit poor aqueous solubility. The intent of such a formulation is to improve the aqueous dissolution properties and ultimately achieve improved bioavailability. Typically, the intent of such systems is to generate a dispersion of amorphous (high energy) drug within the matrix. The presence of the high energy drug form usually improves the dissolution rate. However, these systems are not often physically stable. The drug can crystallize over time, causing the loss of the desired properties and reduced shelf-life. The current invention enhances the physical stability of such formulations, thereby making this type of formulation more feasible.

In the instant invention, PEG 8000 is used as the hydrophilic matrix. Also employed in this formulation is polyvinylpyrrolidone (PVP), which is an example of a hydrophilic, amorphous polymer, and is used to inhibit crystallization. Other hydrophilic, amorphous polymers include hydroxypropylmethylcellulose (HPMC), or other pharmaceutically acceptable hydrophilic, amorphous polymers. Specifically, PVP PF 17 is used within the PEG matrix to inhibit the crystallization of the drug of interest. A range of 1%-95% (w/w) of PVP can be employed, with a range of 1%-15% (w/w) being preferred.

The benefits of incorporating PVP into the PEG matrix are two fold. Firstly, processing PVP can be difficult due to its hygroscopicity. Secondly, when PVP dissolves a viscous layer at the solid-liquid interface forms. This viscous region can hinder dissolution of the drug. Another benefit of adding PVP is an increase in amorphous volume of the polymer matrix where drugs may reside. Since polyethylene glycols tend to be highly crystalline, this increase in amorphous volume could be important for fast dissolution. PVP has the added advantage of having a high Tg, which imparts stabilization of amorphous regions by reducing mobility. Therefore, this invention affords the benefits of the PEG properties in a dispersion along with those of PVP.

A solid (molecular) dispersion comprising an HIV protease inhibiting compound may be prepared by dissolving or dispersing the HIV protease inhibiting compound in a sufficient amount of an organic solvent followed by dispersion into a suitable water soluble carrier. Suitable organic solvents include pharmaceutically acceptable solvents such as methanol, ethanol, or other organic solvents in which the protease inhibitor is soluble. Suitable water soluble carriers include polymers such as polyethylene glycol (PEG), pluronics, pentaeythritol, pentaeythritol tetraacetate, polyoxyethylene stearates, poly-ε-caprolactone, and the like.

The organic solvent (preferably ethanol) may then be evaporated away, leaving the drug dispersed/dissolved in the molten matrix, which is then cooled. The solid matrix has the compound finely dispersed (molecular dispersion) in such a way that dissolution of the drug is maximized, thus improving the bioavailability of a drug exhibiting dissolution rate limited absorption. Ease of manufacturing is also an attribute to this type of formulation. Once the organic solvent is evaporated to yield a solid mass, the mass may be ground, sized, and optionally formulated into an appropriate delivery system. Thus, by improving the dissolution of a poorly water soluble drug, the drug in a suitable carrier may be filled into a gelatin capsule as a solid, or the matrix may potentially be compressed into a tablet.

The delivery system of the present invention results in increased solubility and bioavailability, and improved dissolution rate of the HIV protease inhibiting compound.

Other pharmaceutically-acceptable excipients may be added to the formulation prior to forming the desired final product. Suitable excipients include lactose, starch, magnesium stearate, or other pharmaceutically-acceptable fillers, diluents, lubricants, disintegrants, and the like, that might be needed to prepare a capsule or tablet.

The resulting composition comprising the pharmaceutical compound may be dosed directly for oral administration, diluted into an appropriate vehicle for oral administration, filled into capsules, or made into tablets for oral administration, or delivered by some other means obvious to those skilled in the art. The composition can be used to improve the oral bioavailability and solubility of said HIV protease inhibiting compound.

Total daily dosing of the pharmaceutical compound may be administered to a human in single or divided doses in amounts, for example, from 0.001 to 1000 mg/kg body weight daily, but more usually 0.1 to 50 mg/kg body weight daily. Dosage unit compositions may contain such amounts of submultiples thereof to make up the daily dose. It will be understood, however, that the specific dose level for any particular patient will depend upon a variety of factors including the age, body weight, general health, sex, diet, time of administration, rate of excretion, drugs administered in combination and the severity of the particular disease undergoing therapy.

One type of pharmaceutical compound that may be employed in the practice of the present invention is an HIV protease inhibitor. An example of an HIV protease inhibitor is ABT-538 (ritonavir), the chemical structure of which is represented hereinbelow as a compound of formula I

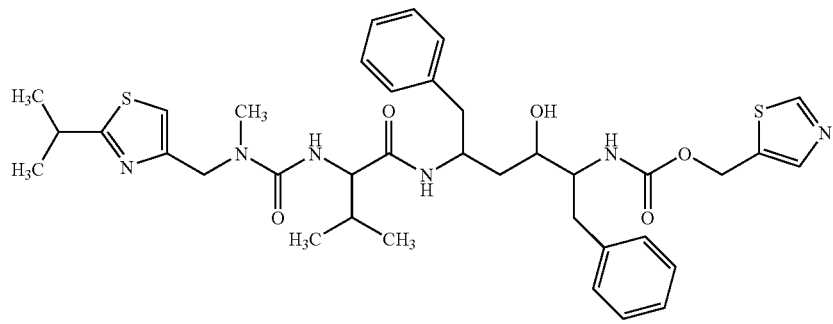

I

A compound of formula I is an HIV protease inhibitor marketed by Abbott Laboratories under the tradename Norvir®, with the common name ritonavir [(2S,3S,5S)-5-(N—(N—((N-methyl-N-((2-isopropyl-4-thiazolyl)-methyl)amino)carbonyl)-L-valinyl)amino-2-(N-((5-thiazolyl)methoxy-carbonyl)-amino)-1,6-diphenyl-3-hydroxyhexane]. This and other compounds as well as methods for preparing same are disclosed in U.S. Pat. Nos. 5,648,497 and 5,541,206, the disclosures of which are herein incorporated by reference.

Additional HIV protease inhibitors which may be formulated into a solid dispersion of the instant invention include compounds of formula II

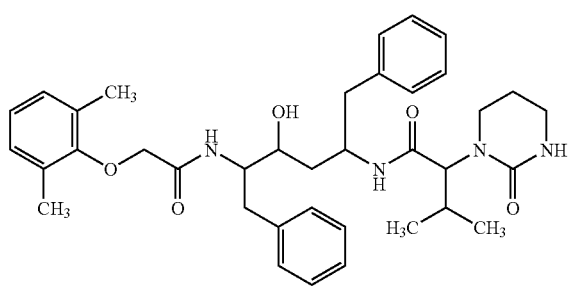

II

A compound of formula II is known as ABT-378 ((2S,3S,5S)-2-(2,6-dimethylphenoxyacetyl)-amino-3-hydroxy-5-(2S-(1-tetrahydropyrimid-2-onyl)-3-methyl-butanoyl) amino-1,6-diphenylhexane). This and other compounds, as well as methods for preparing same, are identified in U.S. Pat. No. 5,914,332, the disclosure of which is herein incorporated by reference.

Other types of pharmaceutical compounds which may be employed in the practice of the present invention include but are not limited to antibacterial agents, antifungal agents such as griseofulvin, chemotherapeutic agents, agents for treating hyperlipidemia such as fenofibrate, and the like.

The following Examples are provided to further illustrate the present invention.

EXAMPLES

Equipment:
DSC

DSC measurements were made using a Mettler DSC 30 unit. Samples (4-7 mg) were sealed in standard 40 µl aluminum crucibles with a single hole punched in the lids. An empty crucible of the same type was used as a reference.

X-ray Powder Diffraction Analysis

An X-ray powder diffraction (XPD) pattern was obtained with a Scintag® XDS 2000 θ/θ diffraction system equipped with a 2 kW normal focus X-ray tube and a liquid nitrogen cooled germanium solid state detector.

Isothermal Calorimetry (TAM)

The recrystallization reactions of 30% ABT-538 in PEG or PEG:PVP (95:5) solid dispersions were monitored via isothermal calorimetry (Thermometric 2277 Calorimeter) at 40° C. Since crystallization is an exothermic process, a positive power output indicates crystallization. The magnitude of the power output at any time is proportional to the rate of crystallization. XPD was used to confirm crystallization.

HPLC

The potency values of all the dispersions as well as the dissolution sample concentrations were determined via HPLC.

The effect of PVP on the crystallization rate of the drug in each dispersion system (drug with polymer) was investigated with the appropriate experimental technique. The results of these studies are provided in FIGS. 1-15.

Three pharmaceuticals of different properties were employed to demonstrate the general applicability of the instant invention. These compounds are identified in Table 1 below:

TABLE 1

Model Compounds

| Property | Compound | | |
|---|---|---|---|
| | ABT-538 | Fenofibrate | Griseofulvin |
| MW (g/mole) | 720.96 | 360.84 | 352.77 |
| $T_m$ (° C.) | 124 | 79 | 218.13 |
| $T_g$ (° C.) | 45.8 | −21.7 | 91 |

Example 1

Dispersion Preparations

A. Ritonavir (ABT-538) Dispersion Preparation:

The samples were prepared by dissolving ABT-538 in a small volume of 200 proof ethanol in a 250 ml round bottom flask. The flask was vortexed and then placed in a water bath maintained at 75° C. The PEG 8000 was added to the hot alcohol solution with continual swirling until the PEG melted. The flask was then attached to a rotary evaporator, immersed in the water bath (75° C.) under vacuum for 15 minutes to remove the ethanol. After the majority of ethanol had evaporated, the flask was immersed in an ice bath for 15 minutes. The contents of the flask were then vacuum dried at room temperature overnight to remove residual alcohol. The dispersion was removed from the flask, gently ground, and sized to 40-100 mesh size. The drug loads used for these dispersions were 10, 20 and 30% w/w.

B. ABT-378 Dispersion Preparation:

The solid dispersion of 30% ABT-538 in 95:5 PEG8000:PVP was prepared by dissolving the ABT-538 and PVP 17 PF in a small volume of 200 proof ethanol in a 250 ml round bottom flask. The remainder of the process was as described above. A 30% ABT-538 dispersion in 85:15 PEG8000:PVP was also prepared similarly as were dispersions of 10 or 20% PVP 17 PF in PEG 8000 without drug.

C. Fenofibrate Dispersion Preparation:

15% Fenofibrate in PEG 8000:

Both fenofibrate and PEG 8000 were sized to 40-100 mesh prior to mixing with a spatula on weighing paper. The mixture was then added to a 25 ml beaker and heated to 85° C. in a water bath until the all the material had melted. The molten solution was then poured onto a chilled X-ray sample holder to rapidly solidify the solution. The solid sample was immediately used to monitor the crystallization rate via X-ray powder diffraction.

15% Fenofibrate in 90:10 PEG 8000:PVP:

Fenofibrate (40-100 mesh) was added to the 90:10 PEG 8000:PVP control dispersion (see above) which was also sized to 40-100 mesh and mixed with spatula on a piece of weighing paper. The mixture was then processed as described above for the 15% fenofibrate dispersion in PEG 8000.

D. Griseofulvin Dispersion Preparation:

15% Griseofulvin in PEG 8000:

Both griseofulvin and PEG 8000 were sized to 40-100 mesh prior to mixing on a weighing paper with a spatula. The sample was then added to an 4 ml stainless steel vessel which was sealed under a $N_2$ atmosphere. The vessel was then immersed into an oil bath maintained at 180° C. The sample was occasionally shaken to mix the molten contents. After 5 minutes the vessel was immersed into a liquid $N_2$ bath for 30 minutes. The contents of the vessel were removed, gently ground and sized to 40-100 mesh.

15% Griseofulvin in 80:20 PEG 8000:PVP:

This dispersion was prepared in a similar manner as describe above for the 15% griseofulvin in PEG 8000 dispersion using the 80:20 PEG8000:PVP control dispersion.

E. Results

Figure 2:
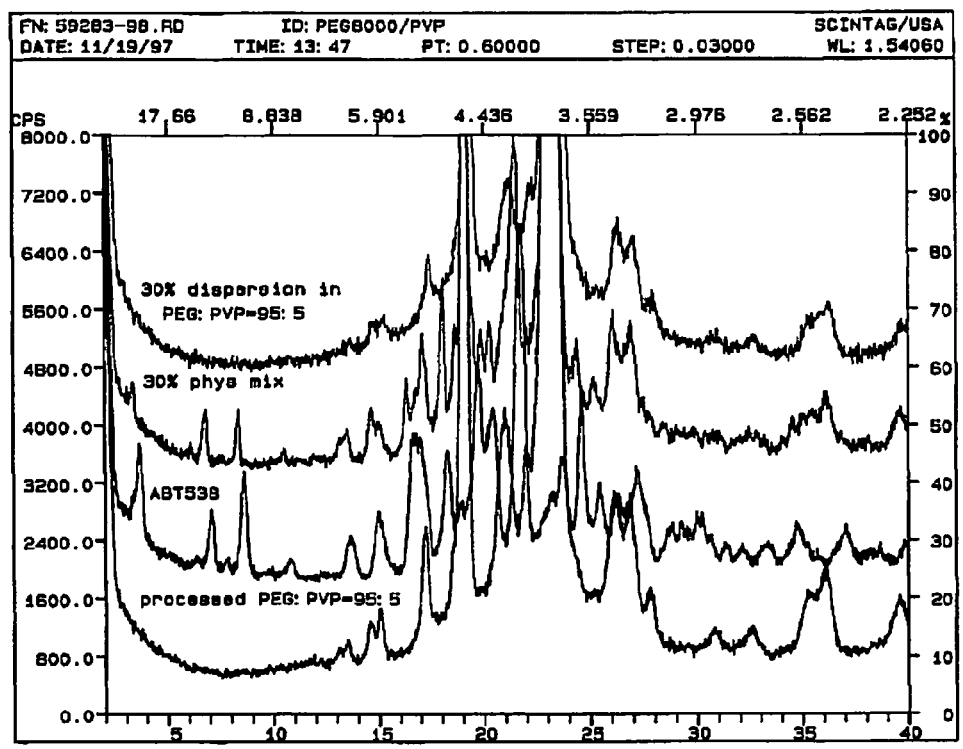
FIG. 2 illustrates the PXD patterns showing that Amorphous ABT-538 can be isolated with a PVP/PEG matrix.
Figure 3:
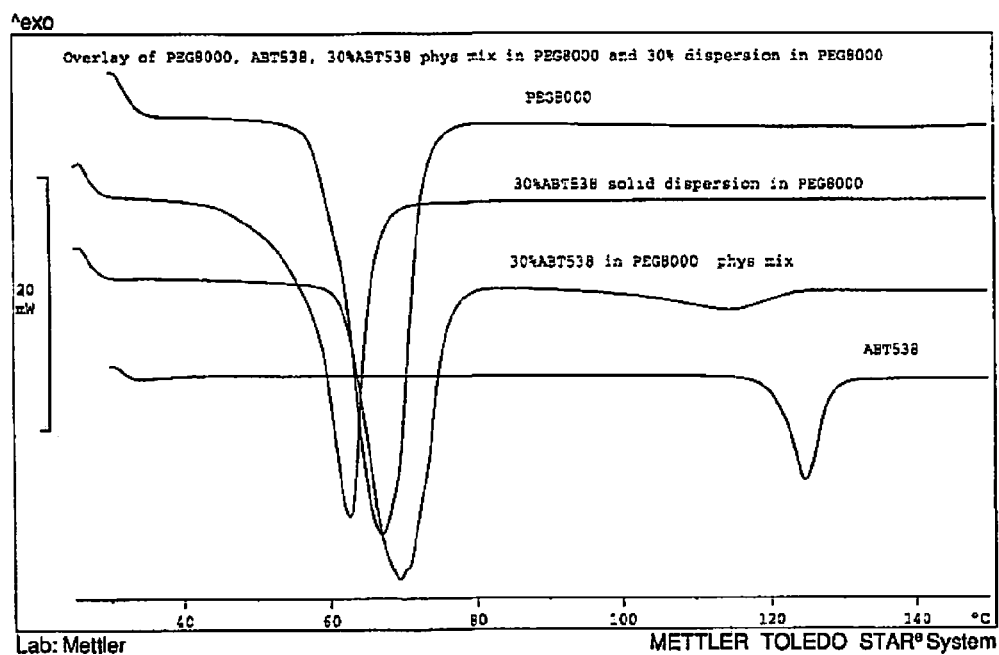
FIG. 3 illustrates the DSC thermograms of PEG, ABT-538, a physical mixture of the two and a solid dispersion. The absence of ABT-538 melting in the dispersion confirms the above PXD data showing amorphous ABT-538 present in the dispersion.
Figure 4:
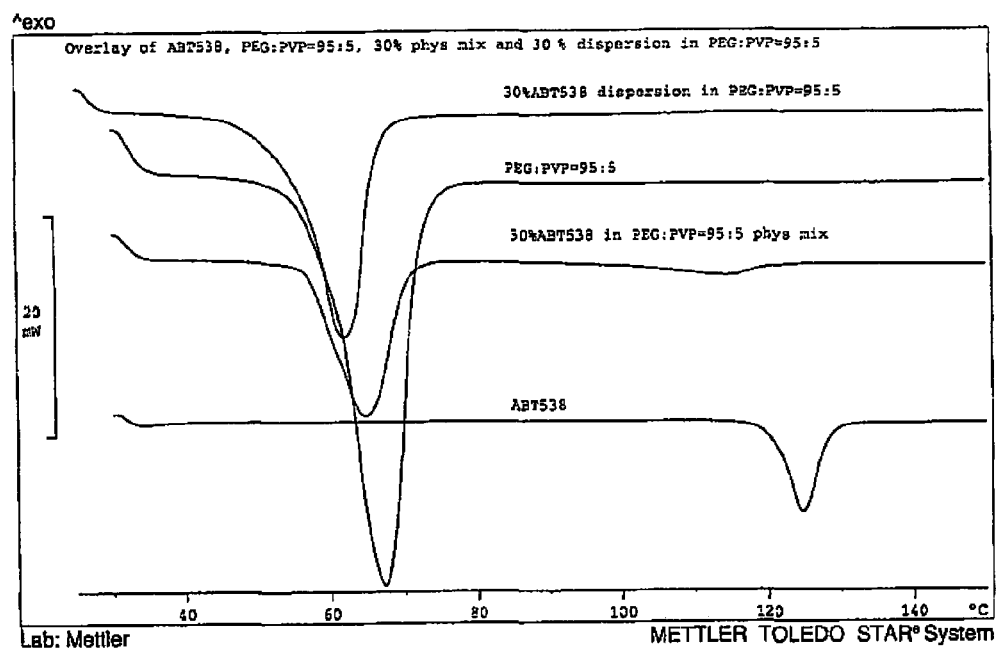
FIG. 4 illustrates the DSC thermograms of PVP/PEG, ABT-538, a physical mixture of the two and a solid dispersion. The absence of ABT-538 melting in the dispersion confirms the above PXD data showing amorphous ABT-538 present in the dispersion.
Figure 5:
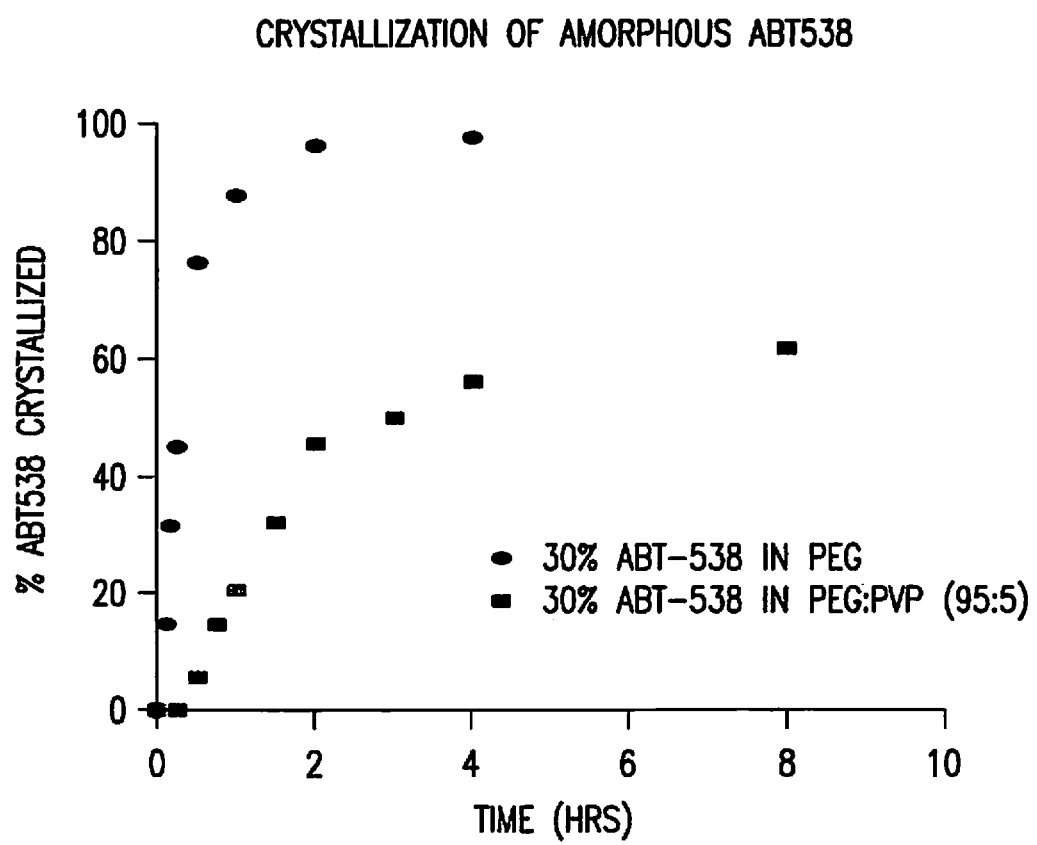
FIG. 5 illustrates the effect of PEG or PVP on the crystallization rate of amorphous ritonavir. The heat of fusion was used to calculate percent crystallized. In the presence of PVP the crystallization rate is slower.
Figure 6:
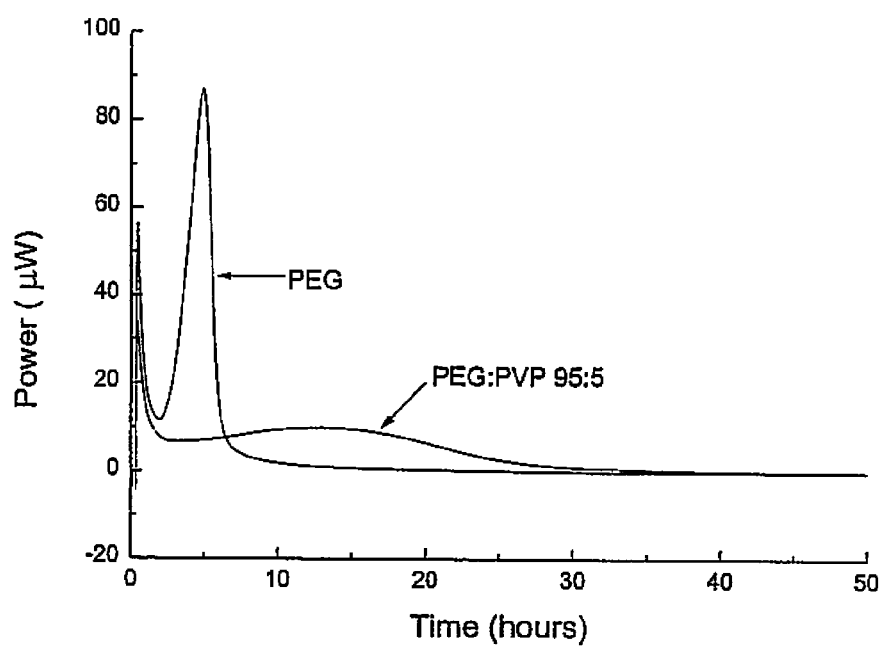
FIG. 6 illustrates the inhibition of crystallization using PVP.

ABT-538:

FIG. 1 shows the X-ray powder diffraction (XPD) pattern of ABT-538, processed PEG 8000, a physical mixture of the two components and the 30% solid dispersion. A similar plot is shown in FIG. 2 with PVP incorporated into the matrix. It is apparent from these figures that ABT-538 is not crystalline within either matrix. FIG. 3 shows the DSC thermograms of ABT-538, PEG8000, the 30% physical mixture and the dispersion. A similar plot is seen in FIG. 4 for the PEG:PVP dispersion. The endotherm associated with drug melting can clearly be discerned from the other components. Thus, it is possible to follow the kinetics of ABT-538 crystallization via DSC measurements. Crystallization kinetics were determined by heating the samples to 85° C., holding them isothermally for predetermined times followed by heating through the melting transition temperature of ABT-538. The heats of fusion were determined and ratioed against the heat of fusion of the drug melting in the physical mixture, giving the fraction crystallized. The percent crystallized as a function of isothermal (85° C.) hold time is shown in FIG. 5. It is clear from this experiment that the presence of PVP within the matrix suppresses the crystallization rate of ABT-538.

The crystallization rate was also followed via the heat associated with crystallization of ABT-538 using a isothermal calorimetry. The shapes and magnitudes of the crystallization peaks in FIG. 6 indicate that ABT-538 crystallizes more readily in the PEG matrix as compared to the PEG:PVP matrix. This stabilizing effect of PVP is also reflected in the times required for complete crystallization (time to reach baseline) which were <10 hours for PEG and >30 hours for PEG:PVP (95:5). These data support the previous DSC results.

Figure 7:
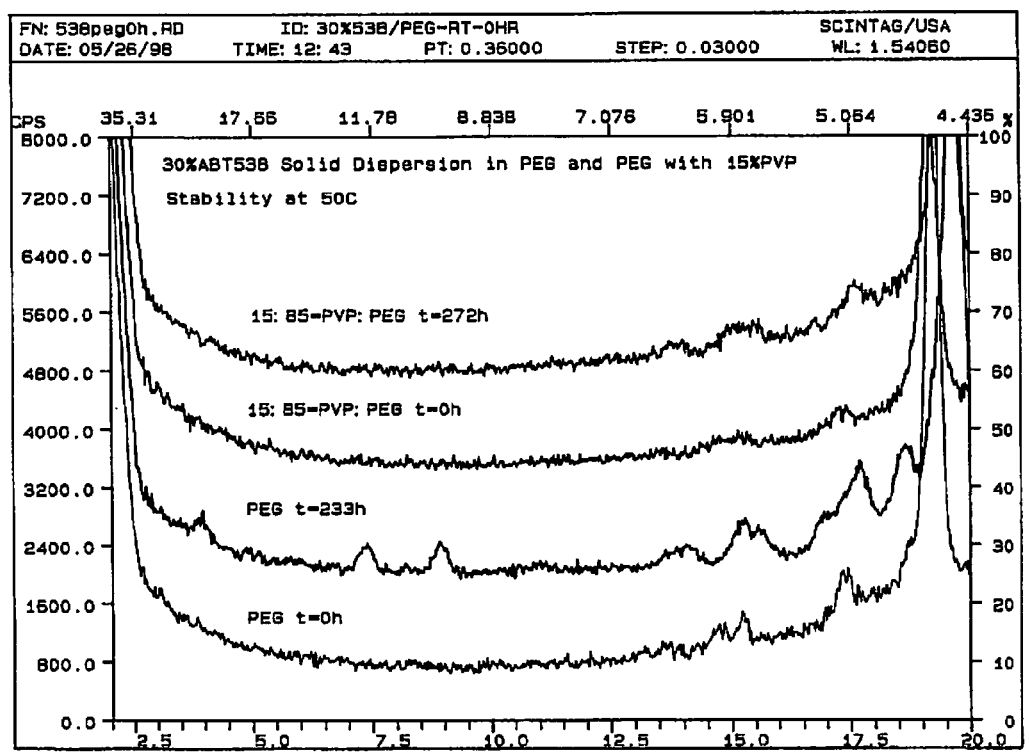
FIG. 7 illustrates PXD patterns of ABT-538 dispersions with and without PVP stored at 50° C. The data demonstrate the improved physical stability of amorphous ABT-538 on storage.

An additional study was performed with a dispersion containing 15% PVP. The samples were held at 50° C. (above the $T_g$ of ABT-538) and X-ray diffraction patterns were measured over time to monitor for the appearance of crystalline ABT-538. FIG. 7 shows that in the presence of PVP, crystalline ABT-538 is not present after 272 hours, while in PEG8000 alone crystalline drug is detected at 233 hours (and before, data not shown).

Figure 8:
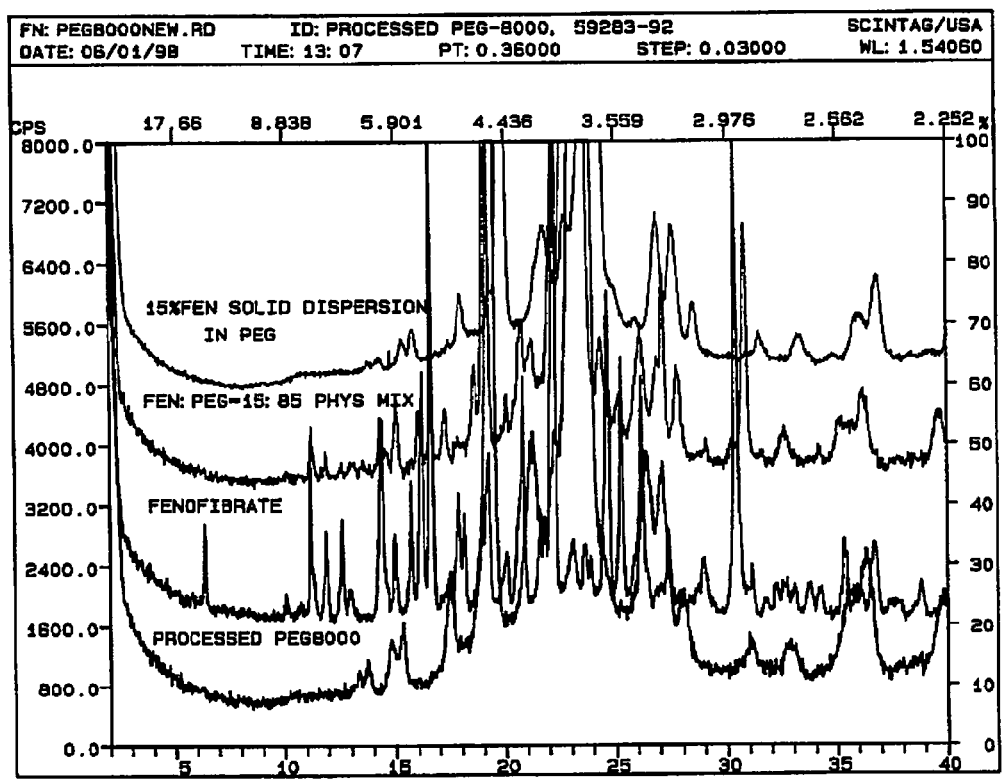
FIG. 8 illustrates PXD patterns of fenofibrate dispersions with and without PVP.
Figure 9:
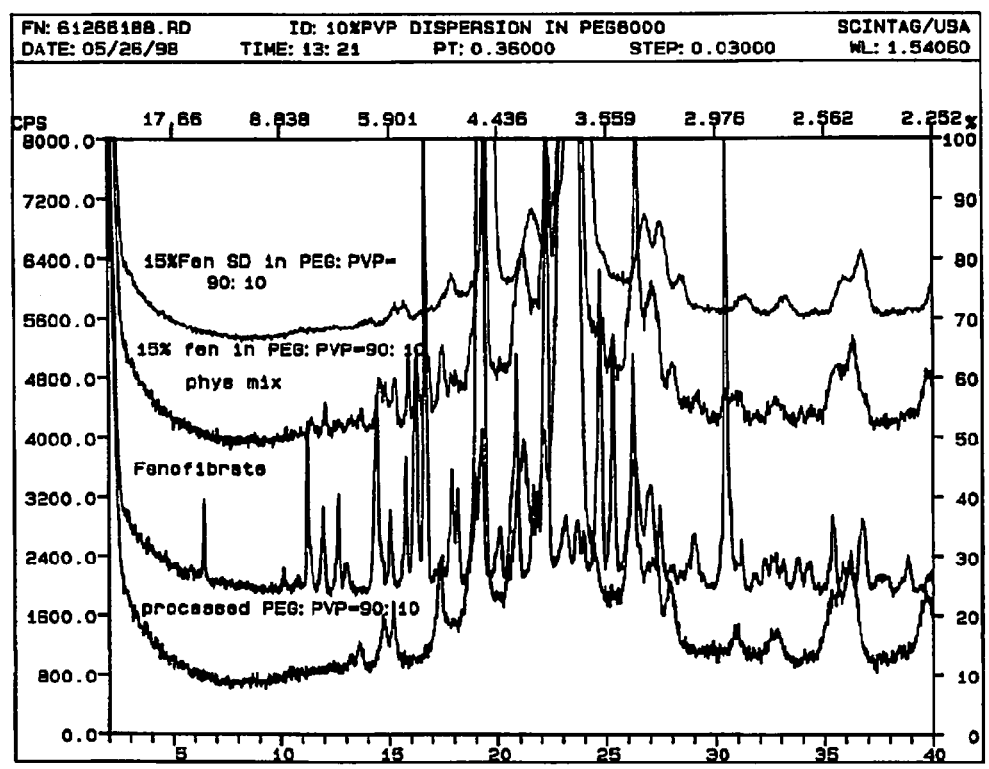
FIG. 9 illustrates PXD patterns of fenofibrate dispersions with and without PVP and PEG.
Figure 10:
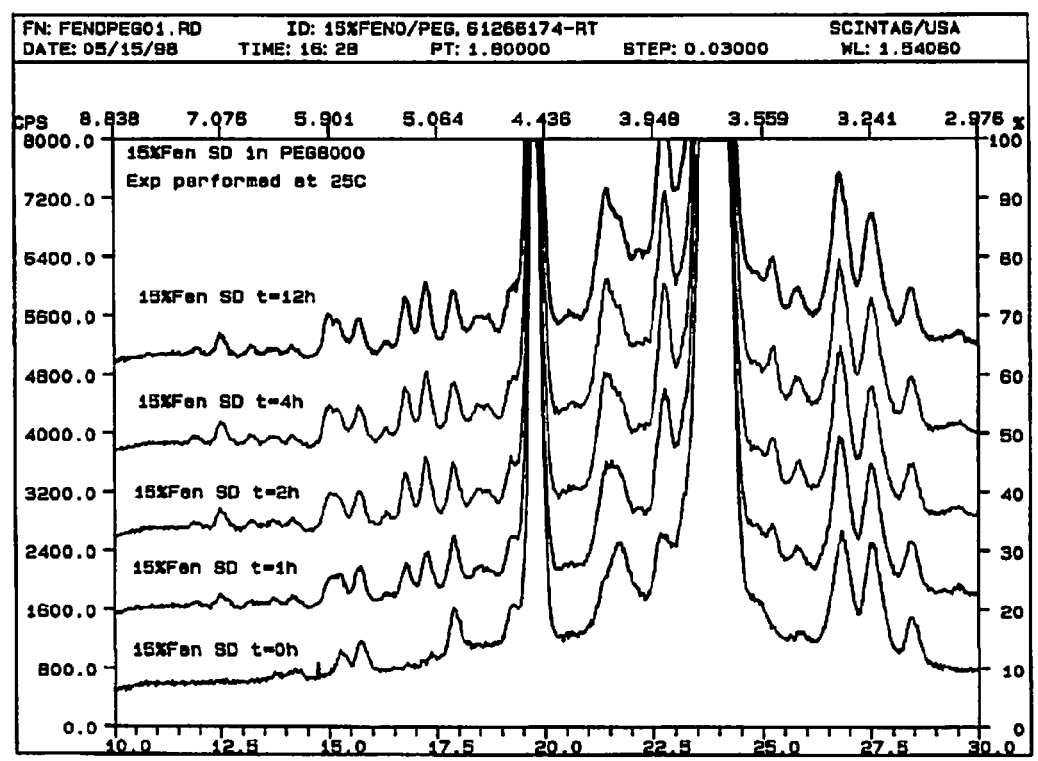
FIG. 10 illustrates PXD patterns of fenofibrate dispersions with and without PEG.
Figure 11:
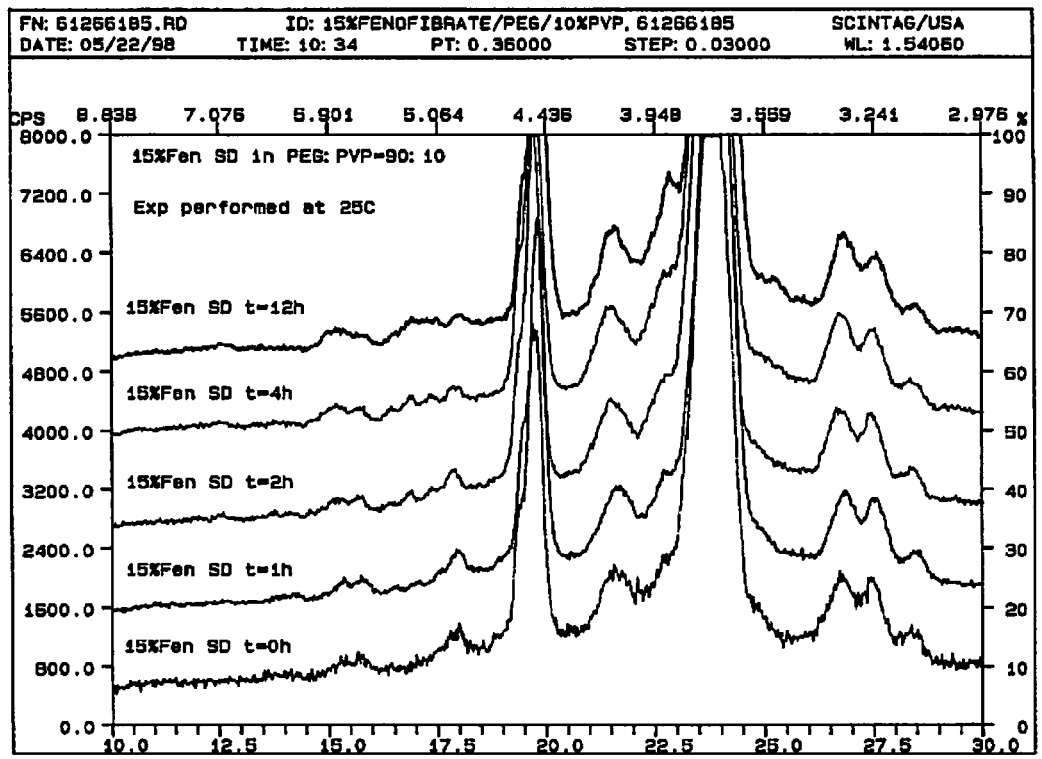
FIG. 11 illustrates PXD patterns of fenofibrate dispersions with and without 10% PVP and PEG.

Fenofibrate:

FIG. 8 shows the XPD patterns of PEG 8000, fenofibrate, a 15% physical mixture and the 15% fenofibrate solid dispersion. The figure illustrates that the fenofibrate is X-ray-amorphous within the matrix. A similar plot with the XPD patterns for the 15% fenofibrate dispersion in a 90:10 PEG 8000:PVP matrix is presented in FIG. 9. Again, the fenofibrate is amorphous. Upon storage at 25° C., the fenofibrate begins to crystallize in the PEG 8000 matrix within 1 hour (FIG. 10). Additional crystallization follows up to 12 hours, when the experiment was terminated. In the presence of PVP (FIG. 11), the fenofibrate does not crystallize in the timeframe of the experiment. This clearly demonstrates the inhibitory effects of PVP on crystallization within the PEG 8000 matrix.

Figure 12:
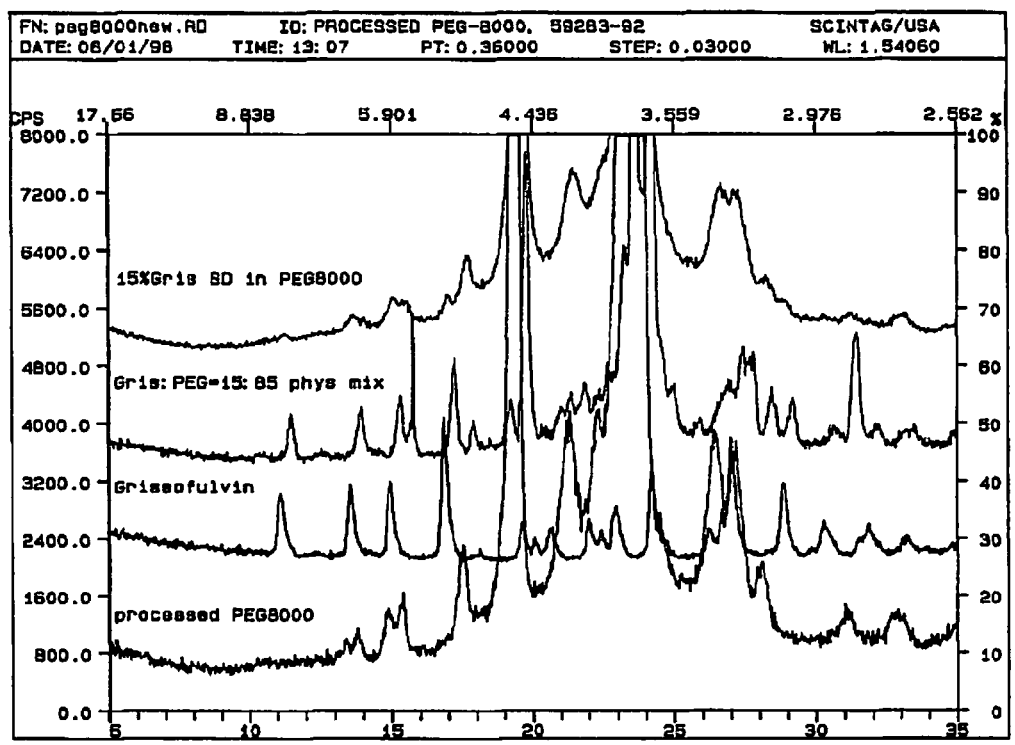
FIG. 12 illustrates PXD patterns of griseofulvin dispersions with and without PEG.
Figure 13:
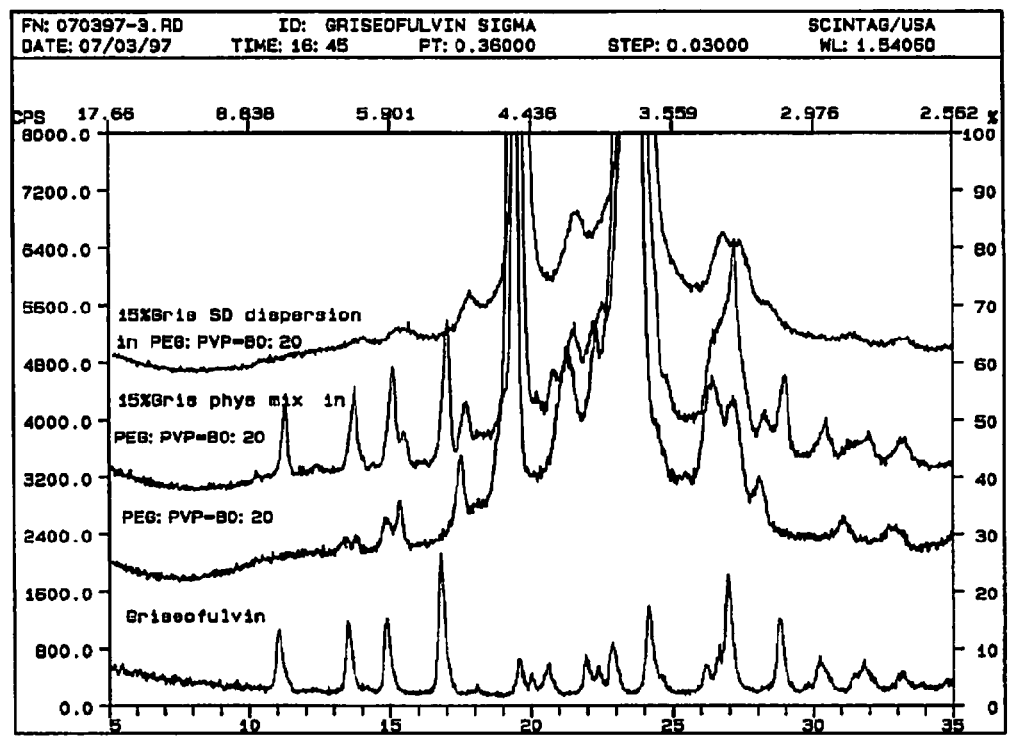
FIG. 13 illustrates PXD patterns of griseofulvin dispersions with and without PEG and PVP.
Figure 14:
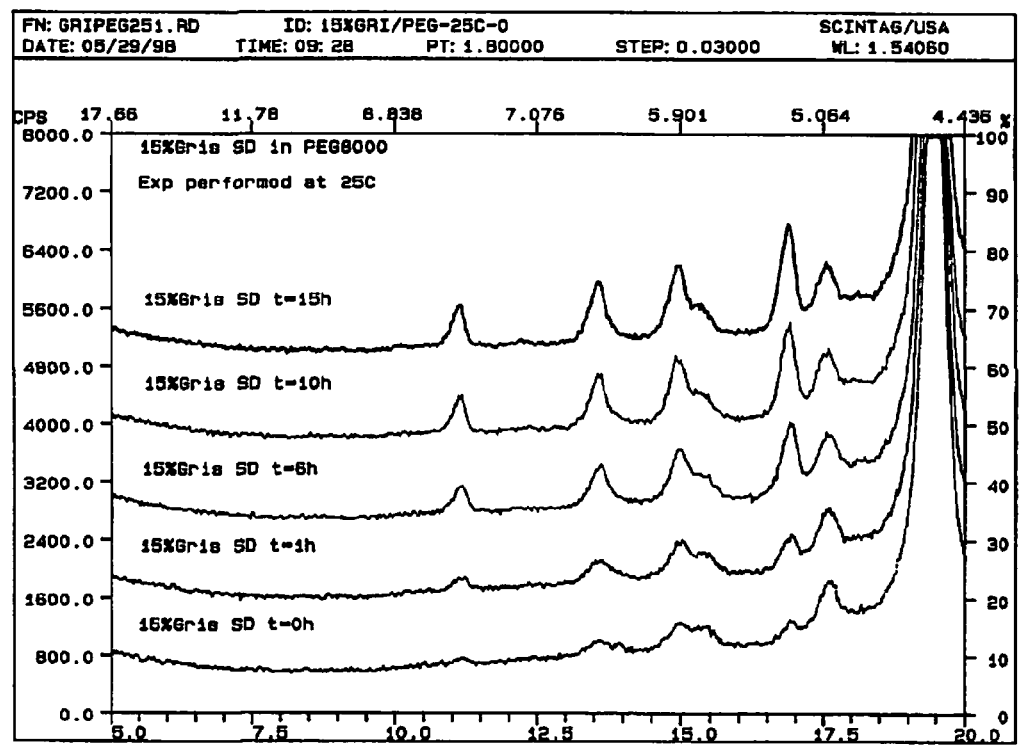
FIG. 14 illustrates PXD patterns of griseofulvin dispersions with and without PEG.
Figure 15:
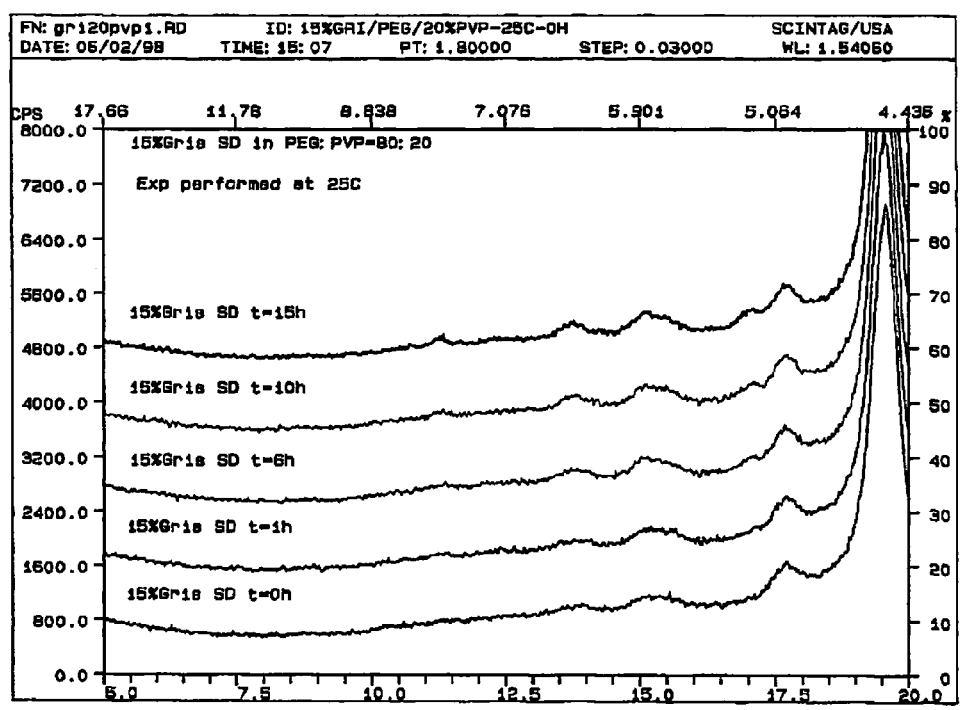
FIG. 15 illustrates PXD patterns of griseofulvin dispersions with and without PEG and PVP.

Griseofulvin:

Similar XPD patterns for the griseofulvin dispersion in PEG 8000 and 80:20 PEG 8000:PVP matrices are shown in FIGS. 12 and 13, respectively. In both instances, amorphous griseofulvin is isolated within the respective matrices. The XPD rate of crystallization experiments show that after one hour at 25° C., griseofulvin begins to crystallize (FIG. 14). However, in the presence of PVP (FIG. 15), crystallization is not observed even after 15 hours under the same conditions. This again demonstrates the inhibitory effects of PVP amorphous drug crystallization within a PEG matrix.

E. Conclusions

The data presented demonstrate that PVP incorporated within a hydrophilic matrix, such as PEG 8000, inhibits crystallization of drug molecules having varying physicochemical properties. Thus, the instant invention has a broad application to development of viable solid dispersion formulations where the high energy amorphous (non-crystalline) form of a drug is desired.

Example 2

Stability of Dispersion in Molten PEG 8000

The stability of the dispersion of ABT-538 in PEG 8000 in the molten state at 70° C. was examined. Individual approximately 5 mg quantities of the dispersion (aged for 6 weeks at room temperature) were placed in 4 ml glass vials. These vials, with the exception of the initial time point, were placed in a 70° C. oven which was sampled at pre-determined intervals, chilled in ice water and placed in the freezer until HPLC analysis. After all samples were collected, they were analyzed for ABT-538 content by HPLC. The HPLC system consisted of a Hitachi AS 4000 autosampler, SP 8800 ternary pump, Applied Biosystems 783 detector, and PE Nelson Data acquisition system. Other chromatographic details included a Regis Little Champ 5 cm C-18 column, a mobile phase consisting of an aqueous solution of 0.1% trifluoroacetic acid in 10 mM aqueous tetramethyl ammonium perchlorate (TMAP)/acetonitrile/methanol (55/40/5). The flow rate was 1 ml/minute, the wavelength of detection was 205 nm, and the injection volume was 100 µl. Standard curves of peak area of ABT-538 vs. concentration in the range of interest were compared with experimentally obtained area counts.

Example 3

Protocol for Oral Bioavailability Studies

Dogs (beagle dogs, mixed sexes, weighing 7-14 kg) are fasted overnight prior to dosing, but are permitted water ad libitum. Each dog receives a 100 µg/kg subcutaneous dose of histamine approximately 30 minutes prior to dosing. Each dog receives a single solid dosage form corresponding to a 5 mg/kg dose of the drug. The dose is followed by approximately 10 milliliters of water. Blood samples are obtained from each animal prior to dosing and at 0.25, 0.5, 1.0, 1.5, 2, 3, 4, 6, 8, 10 and 12 hours after drug administration. The plasma is separated from the red cells by centrifugation and frozen (−30° C.) until analysis. The concentrations of parent drug is determined by reverse phase HPLC with low wavelength UV detection following liquid-liquid extraction of the plasma samples. The parent drug area under the curve is calculated by the trapezoidal method over the time course of the study. The absolute bioavailability of each test composition is calculated by comparing the area under the curve after oral dosing to that obtained from a single intravenous dose. Each capsule or capsule composition is evaluated in a group containing at least six dogs. The values reported are averages for each group of dogs.

We claim:

1. A solid pharmaceutical composition comprising: a molecular dispersion of amorphous ritonavir in a hydrophilic matrix, comprising a water soluble carrier and an amorphous polymer.

2. The composition of claim 1, comprising an amorphous region where said ritonavir resides.

3. The composition of claim 1, further comprising (2S, 3S, 5S)-2-(2,6-dimethylphenoxyacetyl)-amino-3-hydroxy-5-(2S-(1-tetrahydropyrimid-2-only)-3-methyl-butanoyl)amino-1,6-diphenylhexane.

4. The composition of claim 1, wherein crystalline ritonavir is not detectable by X-ray powder diffraction with a 2 kW normal focus X-ray tube after the composition is held at 50° C. for 272 hours.

5. The composition of claim 1, wherein said composition is compressed into a tablet.

6. The composition of claim 1, wherein said composition is encapsulated in a capsule.

7. The composition of claim 1, further comprising a pharmaceutically-acceptable filler, diluent, lubricant, or disintegrant.

8. The composition of claim 2, further comprising (2S, 3S, 5S)-2-(2,6-dimethylphenoxyacetyl)-amino-3-hydroxy-5-(2S-(1-tetrahydropyrimid-2-only)-3-methylbutanoyl)amino-1,6-diphenylhexane.

9. The composition of claim 2, wherein crystalline ritonavir is not detectable by X-ray powder diffraction with a 2 kW normal focus X-ray tube after the composition is held at 50° C. for 272 hours.

10. The composition of claim 2, wherein said composition is compressed into a tablet.

11. The composition of claim 2, wherein said composition is encapsulated in a capsule.

12. The composition of claim 2, further comprising pharmaceutically acceptable filler, diluent, lubricant, or disintegrant.

13. The composition of claim 1, wherein the percentage by weight of amorphous ritonavir in the molecular dispersion is from 10-30% and the water soluble carrier and the amorphous polymer are present in the hydrophilic matrix at a weight ratio selected from 85:15 to 95:5 (water soluble carrier:amorphous polymer).

14. A solid pharmaceutical composition comprising: a molecular dispersion of amorphous ritonavir in a hydrophilic matrix, comprising polyethylene glycol (PEG) and polyvinylpyrrolidone (PVP).

* * * * *